US00PP13038P2

(12) United States Plant Patent

Cosner et al.

(10) Patent No.: US PP13,038 P2

(45) Date of Patent: Oct. 1, 2002

(54) IMPATIENS PLANT NAMED 'TIHOP'

(76) Inventors: Harlan B. Cosner, P.O. Box 173, Broadbent, OR (US) 97414; Susan L. Cosner, P.O. Box 173, Broadbent, OR (US) 97414

( * ) Notice: Subject to any disclaimer, the term of this patent is extended or adjusted under 35 U.S.C. 154(b) by 0 days.

(21) Appl. No.: 09/535,084

(22) Filed: Mar. 23, 2000

(30) Foreign Application Priority Data

Mar. 30, 1999 (CA) ..... 99-1615

(51) Int. Cl.[7] ..... A01H 5/00

(52) U.S. Cl. ..... Plt./317

(58) Field of Search ..... Plt./317

(56) References Cited

U.S. PATENT DOCUMENTS

PP10,260 P * 2/1998 Cosner et al. ..... Plt./317

PP11,532 P * 9/2000 Jonkers ..... Plt./317

OTHER PUBLICATIONS

UPOV ROM GTITM Computer Database, GTI JOUVE retrieval software, 2001/02, citation for 'TiHop'.*

* cited by examiner

*Primary Examiner*—Bruce R. Campell
*Assistant Examiner*—Anne Marie Grünberg
(74) *Attorney, Agent, or Firm*—Ganz Law, PC; Bradley M. Ganz

(57) ABSTRACT

A new and distinct cultivar of '*Impatiens walleriana*' plant named 'TiHop' characterized by large hot pink fully double flowers, flowers that are positioned above or beyond the foliage, good heat tolerance, dark green foliage and mounded, freely branching and dense plant habit.

1 Drawing Sheet

BACKGROUND—FIELD OF INVENTION

The present invention relates to a new and distinct cultivar botanically known as '*Impatiens walleriana*' and by the cultivar name 'TiHop'.

The cultivar of the photograph was developed and selected in a controlled breeding program in a controlled environment in Coquille, Oreg. by the inventors, Harlan Cosner and Sue Cosner, as described herein.

BACKGROUND—DESCRIPTION OF THE PRIOR ART

The closest known cultivar of prior art is named 'Tioga Hot Pink', subject of U.S. Plant Pat. No. 10,260.

COMPARISON

The impatiens plant of the present invention differs from prior plants, namely 'Tioga Hot Pink' in at least the following ways:

1. The plant of the present invention has been shown to perform better in the heat than 'Tioga Hot Pink';
2. The instant cultivar has stronger peduncles than 'Tioga Hot Pink'; and
3. The instant cultivar produces more flowers than 'Tioga Hot Pink'.

These and other characteristics will be apparent to persons skilled in the art.

BACKGROUND—DISCOVERY AND PARENTAGE

The present cultivar was developed by standard cross-pollination. Its seed parent is a semi-double impatiens plant with large hot pink semi-double flowers. This plant was designated 'B-9X-1377' (unpatented) under the inventors' controlled breeding program. The pollen parent is a fully double pollen-producing plant. This plant was designated 'B-9X-201' (unpatented) under the inventors' controlled breeding program. The instant plant is both male and female sterile, compared to the male parent which is only female sterile. The cross was made in the inventors' controlled breeding program, and the first asexual reproduction was made at Broadbent, Oreg. Successive asexually reproduced generations have shown the present invention to be stable. Each asexually reproduced generation has been accomplished using cuttings of lateral stems with leaves.

The traits of the cultivar of the present invention that have been observed in each successive generation of asexual reproduction, and which are unique, are the large hot pink fully double flowers, flowers that are positioned above or beyond the foliage, good heat tolerance, dark green foliage and mounded, freely branching and dense plant habit, and both male and female sterility.

Color references are according to The Royal Horticultural Society Colour Chart, except where general terms of ordinary dictionary significance are used.

DETAILED DESCRIPTION

The following observations, measurements and description of the plants and flowers are based on the environmental and cultural practices at Coquille, Oreg. The following measurements, values and comparisons describe plants grown under a double layer of polyethylene film with temperatures typically ranging from about 55° F. to about 85° F. during the daytime. Night heat was provided by bench top set at 62° F. The individual plants were grown in six-inch Azalea containers in a soiless medium. Plants were liquid fed with high nitrate plus trace elements applied at N level 150 PPM to 2 feed, one leach. Plants started in the last week of June and finished in late September. Light levels were 4,000 to 6,000 ft. candles.

The plant of the present invention has not been observed in all possible environmental and/or cultural conditions. The phenotype may vary significantly with variations in environment such as temperature, light level, humidity and also with cultural practices such as fertility, soil and water quality.

The accompanying photograph illustrates the overall appearance and the flower color of the cultivar of the present invention described herein. The photograph was taken of a mature plant 14 weeks of age, during full inflorescence. There may be variations between the colors in the photograph and the colors in the following description due to, for example, light reflectance, or the amount of blue or red light captured in the film. If such variations occur, the written description shall control.

Parentage: The new cultivar was developed by standard cross-pollination. As noted above, its seed parent was a semi-double with large hot pink flowers; its pollen parent was a pollen-producing double with hot pink flowers.

Propagation:

*Type cutting.*—Lateral stems with leaves were the cuttings used for asexual reproduction.

*Time to initiate roots.*—Approximately 7 to 14 days at 72° F. soil temperature.

Appearance and form of plant:

*Plant form and habit.*—Mounded with a medium vigorous, dense and bushy growing habit. A free-branching habit.

*Plant size.*—Height is about 24 cm, and width is about 35 cm.

*Rooting description.*—The rooting description is characterized by numerous, fibrous and well-branched roots.

*Branching habit.*—Numerous and are self-branching. Stems are strong and freely produced. The number of stems depends upon cultural practices, age of stems used as cuttings and the number of growth buds present on the cutting when stuck.

*Stems.*—Diameter is about 0.6 cm. Internode length is about 2.7 cm. Color is 146A with darker markings of close to 183A, but are hard to determine due to their small size, and are more numerous at the nodes.

*Foliage.*—Leaves are simple, generally symmetrical, abundant, alternate and flat. Shape is ovate with attenuate base, acuminate apex and crenate margin. Leaves alternate along branches. The texture is smooth and satiny.

*Foliage size.*—Size of the largest leaves is about 7 cm in length, and 4.5 cm in width.

*Foliage color.*—Adaxial surface color is darker than 147A, venation color is 147A; abaxial color is 146B, older leaves develop darker markings close to 177A but are hard to determine due to greenish overtones, venation color is close to 148A.

*Petioles.*—Petiole shape is half round with a flat upper surface measuring about 4 mm wide, about 2 mm in depth, and about 4.5 cm in length. Color on the top is 147B with small reddish markings that are hard to determine due to their small size but appear close to 183B. Bottom color is close to 174C at base, darkening to 147B at leaf end.

*Flower size.*—Diameter of the largest flowers is about 4.5 cm, and depth of about 2 cm.

*Flower texture.*—The flower texture is smooth and satiny.

*Flower count.*—Flowers per branch usually number about 10 or more per branch from visible buds to open flowers at a time.

*Natural flowering season.*—Year around under greenhouse conditions, and frost-free period from spring through fall outside. Flowers are continuously produced throughout the flowering season.

*Duration of flower.*—About four to seven days.

*Time to flower.*—About six weeks from a rooted cutting.

*Buds.*—Ovate shape with length of about 1 cm, a width of about 1 cm and depth of about 1 cm. Color of top is 143C, and bottom color is 145B.

*Petal size and shape.*—Shape is obovate with entire margin, cuneate base, and obtuse to retuse apex. Usually two petals fused at base comprise the largest petals, each being about 2 cm wide and 2.5 cm long.

*Petal color.*—Adaxial surface color is close to 66A with a dark base spot close to 59B, some petals have a dark stripe of hard to determine color with reddish overtones that appears close to 61B; abaxial surface is close to 66D.

*Petal count.*—Numerous, usually 20 or more.

*Spur.*—Shape is curved acicular tapering tube with length about 3 cm; sepal end width about 2 mm. Color is close to 181B, slightly darker at base more toward 187B, and slightly lighter at apex more toward 181C.

*Calyx.*—The calyx consists of a single sepal. The sepal shape is elliptic, cuspidate to acuate apex, cordate base, entire margin. Length is about 1.2 cm and width is about 0.9 cm. Adaxial color is 145D with dark base closest to 61A with spots of 61A continuing in a picotee type of edge toward apex which is dark and of undeterminable spot of color which is undeterminable due to it's tiny size. Abaxial color is 145D with purplish markings of close to 66B beginning at base and extending in a picotee type edging toward apex spot which is dark and of undeterminable color due to small size.

*Peduncles.*—Length is about 3 cm and diameter is about 2 mm. Color is 146B with purplish overtones.

*Pedicels.*—Usually numbering two or three, each having a length of about 2.5 cm and diameter of 1.5 mm. Color is 146B to 146C with reddish purple overtones.

*Reproductive organs.*—The plants of the new cultivar are both male and female sterile. No reproductive organs have been found to exist.

*Heat performance.*—The instant plant was grown side by side with 'Tioga Hot Pink' throughout the summer. 'Tioga Hot Pink' produced few flowers, all of which were poorly shaped having numerous undeveloped petaloids in temperatures above 85° F., while the instant plant produced numerous well formed fully double flowers with no noticeable deformities. The instant plant grew equally well at the warmer temperatures as it did at lower temperatures of 75° F. while 'Tioga Hot Pink' grew slowly and poorly at temperatures above 85° F.

*Disease resistance.*—The instant plant has shown good resistance to botrytis.

*Rooting ability.*—Easy, no hormones required.

What is claimed:

1. A new and distinct cultivar of '*Impatiens walleriana*' plant, as illustrated and as described herein.

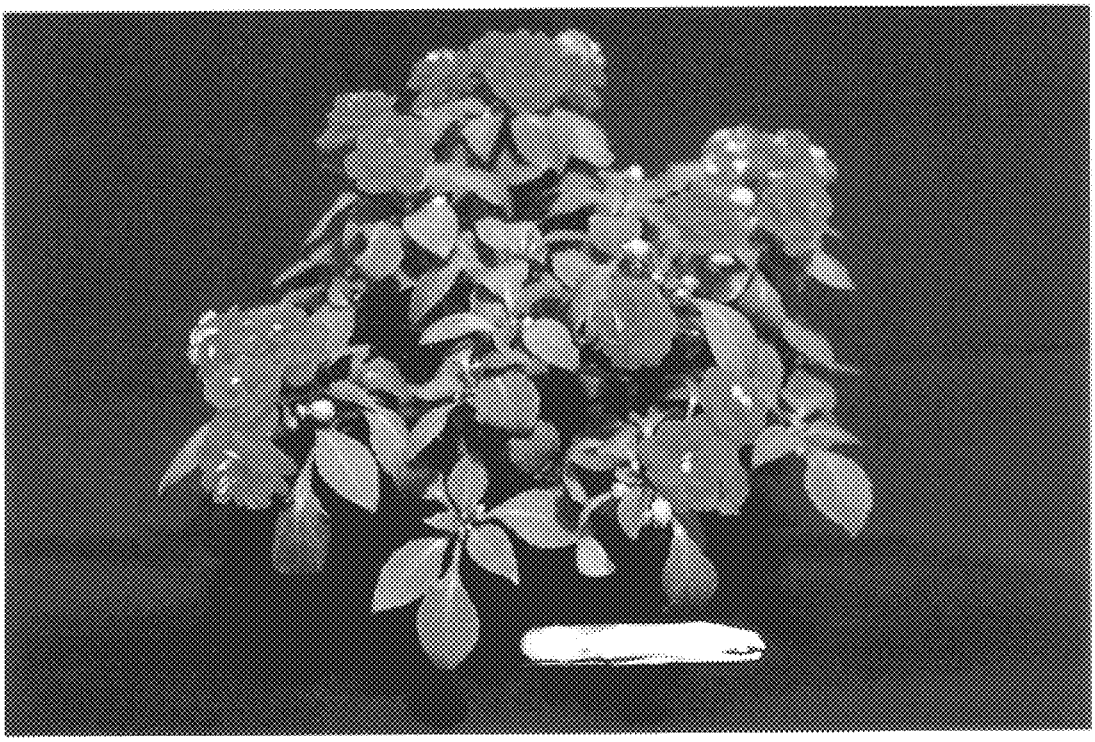

* * * * *